US005626875A

United States Patent [19]

Ballester Rodes et al.

[11] Patent Number: 5,626,875
[45] Date of Patent: May 6, 1997

[54] STABILIZED GALENIC FORMULATIONS COMPRISING AN ACID LABILE BENZIMIDAZOLE COMPOUND AND ITS PREPARATION

[75] Inventors: Montserrat Ballester Rodes; Marinus Van Boven, both of Barcelona, Spain

[73] Assignee: Esteve Quimica, S.A., Barcelona, Spain

[21] Appl. No.: 429,689

[22] Filed: Apr. 27, 1995

[30] Foreign Application Priority Data

Feb. 1, 1995 [ES] Spain ........................... 9500181

[51] Int. Cl.$^6$ ........................... A61K 9/16; A61K 9/50
[52] U.S. Cl. ........................... 424/464; 424/480; 424/451
[58] Field of Search ........................... 424/464, 465, 424/475, 480, 451, 494; 514/925, 926, 927

[56] References Cited

U.S. PATENT DOCUMENTS

| | | | |
|---|---|---|---|
| 4,150,111 | 4/1979 | Warren | 424/35 |
| 4,287,221 | 9/1981 | Tonedachi | 427/3 |
| 4,335,099 | 6/1982 | Funakoshi | 424/32 |
| 4,377,568 | 3/1983 | Chopra | 424/31 |
| 4,470,980 | 9/1984 | Higuchi | 424/232 |
| 5,232,706 | 8/1993 | Coll | 424/475 |
| 5,395,611 | 3/1995 | Jimbow | 424/62 |

FOREIGN PATENT DOCUMENTS

| | | |
|---|---|---|
| 122815 | 10/1984 | European Pat. Off. . |
| 277741 | 8/1988 | European Pat. Off. . |
| 519144 | 12/1992 | European Pat. Off. . |
| 208155 | 6/1983 | Japan . |
| 829055 | 2/1960 | United Kingdom . |
| WO92/22284 | 6/1992 | WIPO . |

OTHER PUBLICATIONS

Coating of Drugs, Up–to–Date Pharmaceutical Technology Series "No. 1", pp. 1 and 2, Jiji Printing Co., Ltd., Dec. 1, 1969.

"Hagers Handbook Der Pharmazeutischen Proxis", vol. 7A, p. 760 (1971 edition).

The United States Pharmacopeia, The National Formulary, p. 2313, 1994.

*Primary Examiner*—Thurman K. Page
*Assistant Examiner*—Sharon Howard
*Attorney, Agent, or Firm*—Ladas & Parry

[57] ABSTRACT

New stable oral pharmaceutical formulations are prepared by covering an inert nucleus with a first layer containing an acid labile benzimidazole compound, a water soluble polymer and non-alkaline reacting pharmaceutical acceptable excipients, a second isolation layer containing a water soluble polymer, pharmaceutical acceptable excipients and a final enteric coating.

14 Claims, No Drawings

STABILIZED GALENIC FORMULATIONS COMPRISING AN ACID LABILE BENZIMIDAZOLE COMPOUND AND ITS PREPARATION

FIELD OF THE INVENTION

The present invention is related to new stable pharmaceutical preparations for oral administration containing a 2[(2-pyridyl)methylsulphinyl]-benzimidazole derivative (hereinafter referred to as "benzimidazole compound") of formula I:

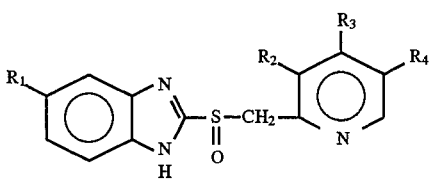

wherein $R_1$ is hydrogen, methoxy or difluoromethoxy, $R_2$ is methyl or methoxy, $R_3$ is methoxy, 2,2,2-trifluoroethoxy or 3-methoxypropoxy, $R_4$ is hydrogen or methyl.

The invention also relates to a method for the manufacture of such preparations and to a method for the treatment of gastrointestinal diseases.

BACKGROUND OF THE INVENTION

The above benzimidazole compounds are very effective drugs for the treatment of gastric and duodenal ulcers, gastroesophageal reflux disease, severe erosive esophagitis, Zollinger-Ellison syndrome and H pylori eradication. However, it is well known that these compounds have poor stability. In the solid state they are susceptible to heat, moisture and light, and in aqueous solution or suspension their stability decreases with decreasing pH. The degradation of these compounds is catalyzed by acidic reacting compounds.

Pharmaceutical preparations containing acid-labile compounds have to be subcoated in order to avoid a reaction between the active ingredient and the outer acidic enteric coating which reaction—if occurring—would result in degradation, destabilization and consequently discoloration of the active ingredient.

The use of a barrier layer to protect the pharmaceutical from degradation caused by an enteric coating is well known from the prior art. Nevertheless, it is not possible to use conventional enteric coatings in a conventional way for acid labile benzimidazole compounds since decomposition takes place and the preparations become discolored and lose the active ingredient content with time. Prior art partially avoids the above mentioned stability problem by including an alkaline salt form of the benzimidazole compound or incorporating an alkaline reacting compound into an enteric coated preparation (U.S. Pat. No. 4,786,505, U.S. Pat. No. 5,232,706, EP 237200, EP 124495), the alkaline reacting compound being present within or on the surface of the nucleus together with the benzimidazole compound. Also the alkaline reacting compound is being used in the composition of a second isolation layer to ensure stability of these forms. Thus, the association of an alkaline substance to the neutral form of the benzimidazole compound is taught in order to improve the stability of the active compound, especially for solid dosage forms, and enteric coating is recommended. Nevertheless, a superior stability of the preparations would be required to ensure the stability of the drug for long term storage.

OUTLINE OF THE INVENTION

According to the present invention high stability solid preparations containing a benzimidazole compound of formula I are obtained. The new galenic formulations do not contain alkaline reacting compounds. It has been found that it is not necessary to create an alkaline environment into the enteric coated preparation. The obtained new preparations have a significantly enhanced stability for long-term storage, much higher than the known preparations, avoid discoloration and loss of purity and, thus are more suitable for pharmaceutical use.

The new preparation is characterized in that to an inert sugar/starch spherical core, a first layer is applied containing a mixture of the benzimidazole compound of formula I as active ingredient, a water soluble inert polymer and non-alkaline reacting pharmaceutical acceptable excipients, followed by a second isolation layer formed by water soluble polymers and compatible excipients. Finally a third layer consisting of an enteric coating is applied. The core, the process conditions and the excipients have been selected in order to obtain the required coating efficiency for each layer.

The resulting new preparation is resistant to dissolution in acid media being stable for passage through the gastric juice, and dissolves rapidly in a neutral to alkaline media, the conditions in the proximal part of the small intestine. In fact, the acid resistance, tested as per US Pharmacopoeia, demonstrated that after 2 hours the total amount of the benzimidazole remained intact and that upon changing the pH to 6.8, after 30 minutes all the benzimidazole was dissolved (tested as per US Pharmacopoeia).

DETAILED DESCRIPTION OF THE INVENTION

In a fluidized bed apparatus, uniform spherical inert cores (composition as per US Pharmacopoeia) are coated with a first layer consisting of the acid labile benzimidazole compound, an inert water soluble polymer such as hydroxypropylmethylcellulose or hydroxypropylcellulose, and talc. The second layer consists of an inert water soluble polymer such as hydroxypropylmethylcellulose or hydroxpropylcellulose, talc and a pigment such as titanium dioxide. The third and enteric coating layer consists of an enteric coating polymer such as co-polymerized methacrylic acid/methacrylic acid methyl esters, a plasticizer such as triethylcitrate or similar plasticizers, and talc.

The layers are applied by conventional fluidized bed coating techniques using aqueous solutions or dispersions.

The active ingredients can be administered in the same dosages and according to the same protocol as the corresponding already marketed commercial dosage forms.

For oral administration, the final dosage may take the form of capsules containing the pellets, or pellets compressed into a tablet.

The dose as the benzimidazole compound lies within the range of about 1 mg to 100 mg/kg/day, adjusted to individual patients needs and for as long as clinically indicated.

The invention is described in detail in the following examples:

EXAMPLE 1

In 3440 g of deionized water 436 g of Omeprazole (I; $R_1$=-OCH$_3$, $R_2$=CH$_3$, $R_3$=-OCH$_3$, $R_4$=CH$_3$), 444 g of hydroxypropylmethylcellulose and 118 g of talc are dispersed.

3010 g of inert uniform sugar/starch spheres (composition according to US Pharmacopoeia) are introduced into a fluidized bed apparatus and the previous obtained dispersion is sprayed on the spheres. After spraying, the spheres are dried before applying the second layer.

In 2365 g of deionized water, 355 g of hydroxypropylmethylcellulose, 43 g of talc and 43 g of titanium dioxide are dispersed and the resulting aqueous dispersion is sprayed on the spheres obtained in the previous step. After spraying, the spheres are dried before applying the third enteric coating layer.

In 1890 g of deionized water, 1950 g of methacrylic acid copolymer (US Pharmacopoeia, type C aqueous dispersion), 98 g of triethylcitrate and 98 g of talc are dispersed, and the resulting aqueous dispersion is sprayed on the spheres obtained in the previous step. After applying this final enteric coating layer the spheres (pellets) are dried.

The pellets thus obtained were stored in closed polyethylene bags within a closed cardboard fibre container and also in closed glass containers and submitted to so called accelerated conditions, that is 40° C. and 75% relative humidity. At the same time pellets obtained from Prilosec® capsules (Merck/Astra trademark) were stored in identical containers and submitted to the same conditions. The results of the test under accelerated conditions are summarized in tables 1, 2 and 3. They demonstrate a superior stability over the already authorized product on the market.

TABLE 1

| COLOR OF THE PELLETS | | | |
|---|---|---|---|
| | AT THE START | 1 MONTH | 3 MONTHS |
| Pellets (I) - Fiber container | A | A | D |
| Pellets (I) - Glass container | A | A | B |
| Prilosec - Fiber container | A | C | F |
| Prilosec - Glass container | A | A | E |

A: White
B: Pinkish white
C: faint brown
D: light brown
E: brown
F: Deep brown

TABLE 2

| OMEPRAZOLE PURITY* | | | |
|---|---|---|---|
| | AT THE START | 1 MONTH | 3 MONTHS |
| Pellets (I) - Fiber container | 99,5% | 98,8% | 52% |
| Pellets (I) - Glass container | 99,5% | 98,7% | 97,9% |
| Prilosec - Fiber container | 96,1% | 85,2% | 1% |
| Prilosec - Glass container | 96,1% | 96,2% | 1% |

*Analyzed as per HPLC, described in Pharmaeuropa, Vol. 4, n° 2, June 1992 and expressed as direct area percentage.

TABLE 3

| OMEPRAZOLE RECOVERY AFTER US DISSOLUTION TEST | | |
|---|---|---|
| | 1 MONTH | 3 MONTHS |
| Pellets (I) - Fiber container | 96,8% | 9,2% |
| Pellets (I) - Glass container | 99,9% | 73,8% |
| Prilosec - Fiber container | 21,3% | <<1% |
| Prilosec - Glass container | 84,5% | <<1% |

EXAMPLE 2

In 580 g of deionized water, 75 g of Lansoprazole (I; $R_1$=H, $R_2$=$CH_3$, $R_3$=2,2,2-trifluoroethoxy, $R_4$=H), 70 g of hydroxypropylmethylcellulose and 18.5 g of talc are dispersed.

490 g of inert uniform sugar/starch spheres are introduced into a fluidized bed apparatus and the previous obtained dispersion is sprayed on the spheres. The process continues in the same manner as in Example 1 spraying the second layer and the third enteric coating layer. These two dispersions have the following composition:

Second layer: 350 g of deionized water, 52 g of hydroxypropylmethylcellulose, 7 g of talc and 7 g of titanium dioxide.

Enteric coating layer: 280 g of deionized water, 290 g of a USP methacrylic acid copolymer (type C aqueous suspension), 13 g of triethylcitrate and 13 g of talc.

The pellets obtained were stable and showed a similar profile as the ones from example 1.

What is claimed is:

1. A stable oral pharmaceutical preparation containing an acid labile benzimidazole compound of formula I:

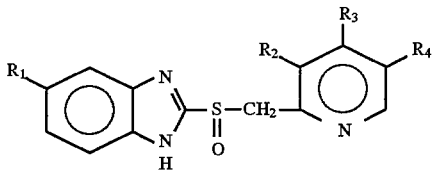

wherein $R_1$ is hydrogen, methoxy or difluoromethoxy; $R_2$ is methyl or methoxy; $R_3$ is methoxy, 2,2,2-trifluoroethoxy or 3-methoxypropoxy and $R_4$ is hydrogen or methoxy, which comprises:

(a) a nucleus formed by an inert core, the acid labile benzimidazole compound of formula I, a non-alkaline inert water soluble polymer and non-alkaline reacting pharmaceutical acceptable exicipients;

(b) an inert non-alkaline coating disposed on said nucleus, formed by a non-alkaline water soluble polymer and non-alkaline pharmaceutical excipients, and (c) an outer layer disposed on the previous coating comprising an enteric coating.

2. A preparation according to claim 1 wherein the water soluble polymer comprises hydroxypropylmethylcellulose or hydroxypropylcellulose.

3. A process for the preparation of a stable oral pharmaceutical preparation containing an acid labile benzimidazole compound of formula I as active ingredient

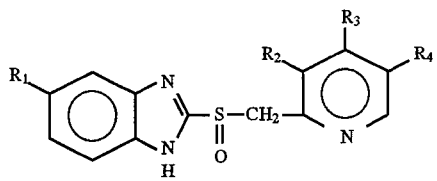

wherein $R_1$ is hydrogen, methoxy or difluoromethoxy; $R_2$ is methyl or methoxy; $R_3$ is methoxy, 2,2,2-trifluoroethoxy or 3-methoxypropoxy; and $R_4$ is hydrogen or methyl, which comprises:

(a) preparing a nucleus formed by an inert core, the acid labile benzimidazole, compound of formula I, a non-alkaline inert water soluble polymer and non-alkaline reacting pharmaceutical acceptable excipients;

(b) coating said nucleus with an inert non-alkaline layer formed by a non-alkaline water soluble polymer and non-alkaline pharmaceutical acceptable excipients; and (c) coating the coating of step (b) with an enteric coating.

4. A method for the treatment of gastrointestinal diseases comprising administering capsules or tablets containing the stable oral pharmaceutical preparation according to claim 1.

5. The preparation according to claim 1 wherein the enteric coating comprises a gastric resistant polymer, a plasticizer and pharmaceutical acceptable excipients.

6. The preparation according to claim 5 wherein the gastric resistant polymer is copolymerized methacrylic acid/methacrylic acid methyl esters.

7. The preparation according to claim 5 wherein the plasticizer is triethylcitrate.

8. The preparation according to claim 1 wherein the non-alkaline inert water soluble polymer of the nucleus is hydroxypropylmethylcellulose or hydroxypropylcellulose.

9. The preparation according to claim 1 wherein the non-alkaline water soluble polymer of the inert coating is hydroxypropylmethylcellulose or hydroxypropylcellulose.

10. The preparation according to claim 1 wherein the inert coating further comprises a pigment.

11. The preparation according to claim 10 wherein the pigment is titanium dioxide.

12. A stable oral pharmaceutical preparation containing an acid labile benzimidazole compound of formula I:

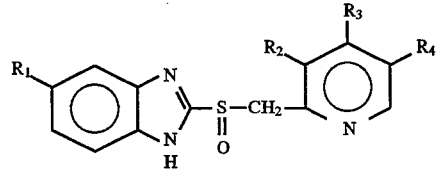

wherein $R_1$ is hydrogen, methoxy or difluoromethoxy, $R_2$ is methyl or methoxy, $R_3$ is methoxy, 2,2,2-trifluoroethoxy or 3-methoxypropoxy; and $R_4$ is hydrogen or methyl, which consists essentially of:

(a) a nucleus formed by an inert core, the acid labile benzimidazole compound of formula I, a non-alkaline inert water soluble polymer and non-alkaline reacting pharmaceutical acceptable exicipients;

(b) an inert non-alkaline coating disposed on said nucleus, formed by a non-alkaline water soluble polymer and non-alkaline pharmaceutical excipients, and (c) an outer layer disposed on the previous coating comprising an enteric coating.

13. A stable oral pharmaceutical preparation containing an acid labile benzimidazole compound of formula I:

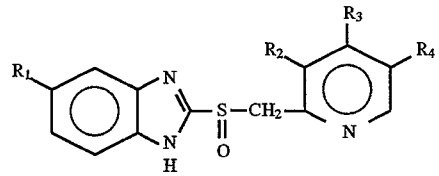

wherein $R_1$ is methoxy, $R_2$ is methyl, $R_3$ is methoxy and $R_4$ is methyl which consists essentially of:

(a) a nucleus formed by an inert core, the acid labile benzimidazole compound of formula I, hydroxypropyl methylcellulose and talc;

(b) an inert non-alkaline coating disposed on said nucleus, formed by hydroxypropylmethylcellulose, talc and titanium dioxide and (c) an enteric coating disposed on the coating of (b) consisting essentially of methacrylic acid copolymer, triethylcitrate and talc.

14. A stable oral pharmaceutical preparation containing an acid labile benzimidazole compound of formula I:

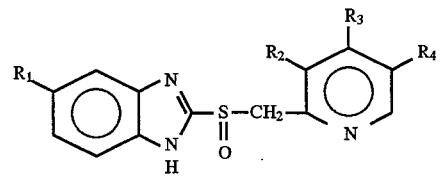

wherein $R_1$ is hydrogen, $R_2$ is methyl, $R_3$ is 2,2,2-trifluoroethoxy and $R_4$ is hydrogen which consists essentially of:

(a) a nucleus formed by an inert core, the acid labile benzimidazole compound of formula I, hydroxypropyl methylcellulose and talc;

(b) an inert non-alkaline coating disposed on said nucleus, formed by hydroxypropylmethylcellulose, talc and titanium dioxide and (c) an enteric coating disposed on the coating of (b) consisting essentially of methacrylic acid copolymer, triethylcitrate and talc.

* * * * *